(12) United States Patent
Kenny (10) Patent No.: US 8,616,767 B2
(45) Date of Patent: Dec. 31, 2013

(54) EQUINE FOOT IMAGING PLATFORM AND METHOD

(76) Inventor: Martin D. Kenny, Carthage, NC (US)

(*) Notice: Subject to any disclaimer, the term of this patent is extended or adjusted under 35 U.S.C. 154(b) by 292 days.

(21) Appl. No.: 13/269,035

(22) Filed: Oct. 7, 2011

(65) Prior Publication Data

US 2013/0089179 A1 Apr. 11, 2013

(51) Int. Cl.
*H05G 1/02* (2006.01)
*G03B 42/04* (2006.01)
*G03B 42/02* (2006.01)
*G01N 23/083* (2006.01)

(52) U.S. Cl.
USPC ......... 378/208; 378/177; 378/179; 250/491.1

(58) Field of Classification Search
USPC ........... 378/62, 167, 177, 179, 180, 189, 190, 378/192, 195–197, 204, 205, 207, 378/208–210; 250/440.11, 442.11, 358.1, 250/360.1, 370.08, 370.09, 371, 491.1, 250/526; 600/407, 415
See application file for complete search history.

(56) References Cited

U.S. PATENT DOCUMENTS

| | | | |
|---|---|---|---|
| 2,499,098 A * | 2/1950 | Howe | 168/48.2 |
| 3,095,186 A | 6/1963 | Sondy | |
| 4,430,802 A | 2/1984 | Cole | |
| 7,003,344 B2 * | 2/2006 | Bolas et al. | 600/410 |
| 7,704,020 B1 | 4/2010 | Stengel | |
| 2013/0129056 A1 * | 5/2013 | Ovnicek | 378/208 |

* cited by examiner

*Primary Examiner* — Anastasia Midkiff
(74) *Attorney, Agent, or Firm* — Coats and Bennett PLLC (57) ABSTRACT

An imaging platform assembly is used to support a hoofed animal, especially horses, during a foot imaging process. The platform assembly includes a platform and flush mounted turntables that allow the animal's feet to rotate under the animal's power, thereby allowing the animal to assume a more natural stance. By allowing this rotation, the animal less likely to cause trouble during the imaging process. One or more of the turntables include a slot that is configured to support an image capturing device, such as an x-ray cartridge. One to all of the animal's feet may be on turntables, depending on the platform configuration.

18 Claims, 6 Drawing Sheets

EQUINE FOOT IMAGING PLATFORM AND METHOD

BACKGROUND

The present invention generally relates to pass-through imaging of equine (e.g., horse) feet, and more particularly relates to an equine foot imaging platform that supports the foot being imaged on a turntable that is rotatable by the equine, and related methods.

It is often desirable to image an equine animal's foot for various reasons. For example, it may be desirable to image a horse's foot to determine a proper shoe configuration and/or or to diagnose a disease or other malady. Previous methods for imaging typically include having the horse place the foot on a short post or other pedestal, and then imaging the foot using a portable x-ray source, with the corresponding imaging cartridge arranged behind the foot to be imaged. Typically, the x-ray source's cone of emission is centered some distance above the bottom of the x-ray source unit; however, this cone should be normal the imaging cartridge and generally horizontal for the best results. Thus, if the horse is standing directly on the ground, the x-ray source is too high; as such, the horse's foot is placed on the pedestal in order to raise it. However, farriers and veterinarians frequently experience difficulty both in getting the horse to place the foot on the pedestal and in having the horse remain stationary during the imaging. Further, applicant has discovered that the use of a pedestal results in the horse loading the foot in an unnatural way. As such, there remains a need for alternative approaches to equine foot imaging.

SUMMARY

The present invention, in one embodiment, provides a method of imaging an equine foot that comprises supporting both the front feet or both the rear feet of an equine animal on respective rotatable first and second turntables. The first and second turntables are mounted to a common platform and rotatable independently of each other about respective rotational axes. The animal is allowed to rotate at least one of the turntables. The first turntable has an upwardly open first slot therein. The method includes placing an image capture device in the first slot of the first turntable. The method includes thereafter imaging the foot disposed on the first turntable by passing radiation through the foot to the image capture device. The second turntable may also have an upwardly open second slot therein, and the method may further comprise: 1) placing an image capture device in the second slot; and 2) thereafter, imaging the foot disposed on the second turntable by passing radiation through the foot to the image capture device in the second slot. The platform may have a generally planar upper surface, and the first and second turntables may have respective upper surfaces that are disposed generally flush with the upper surface of the platform. One, two, three, or all four of the animal's feet may be on turntables, depending on the embodiment. In some embodiments, a panel in the platform may be removed to expose a recess, with the radiation source being disposed in that recess prior to the passing of radiation through the foot.

In another embodiment, the present invention provides an equine imaging platform assembly configured to support at least two feet of an equine animal. The platform assembly comprises a platform having a generally planar upper surface with first and second turntable recesses therein. A first turntable is disposed in the first recess and rotatably coupled to the platform for rotation about a first rotational axis. The first turntable has a first hoof-engaging turntable upper surface disposed generally flush to the upper surface of the platform. A second turntable is disposed in the second recess and rotatably coupled to the platform for rotation about a second rotational axis. The second turntable has a second hoof-engaging turntable upper surface disposed generally flush to the upper surface of the platform. The first and second rotational axis are spaced from one another and oriented generally normal to the platform upper surface and the first and second turntables are rotatable independently of each other. The first and second turntables may be configured to be readily removable from the corresponding bearing assemblies without tools. The first and second turntables may be configured to support at least 600 pounds each. The platform upper surface and the first and second turntable upper surfaces may have non-slip layers thereon. The first turntable upper surface has an upwardly open first slot therein sized and configured to receive an image capturing device. The first slot may be offset from the first rotational axis. The platform may comprise first and second sections hingedly coupled together, with the first and second recesses disposed in the first and second sections respectively. The platform may be sized to support the front feet of the equine animal when the turntables are supporting the rear feet of the equine animal. The platform may include at least one removable panel disposed in spaced relation to the turntables.

Of course, the present invention is not limited to the above features and advantages. Indeed, those skilled in the art will recognize additional features and advantages upon reading the following detailed description, and upon viewing the accompanying drawings.

DETAILED DESCRIPTION

The present invention relates to an imaging platform assembly that is used to support a hoofed animal, especially equines (e.g., horses, donkeys, zebras, mules), during a foot pass-through imaging process. The platform assembly includes turntables that allow the animal's feet to rotate, thereby allowing the animal to assume a more natural stance. By allowing this rotation, the animal is less likely to cause trouble during the imaging process.

Initially, it should be appreciated that the following discussion, for simplicity, will generally be in the context of using one or more embodiments of an illustrative equine foot imaging platform to image the foot of a horse 3. However, the present invention is not so limited, and can be used for any hoofed animal. Further, the following discussion will be primarily in the context of use with a portable x-ray source 10 and a conventional x-ray film cartridge 12; however, other imaging equipment may be used. For example, some x-ray systems use a detector array rather than a traditional film cartridge 12. For ease of reference, both of the film and the detector array are considered to be image capture devices 12. Other imaging systems may use other types of radiation, rather than x-rays, to create an image of the interior of the foot 5, including the hoof, via transmission through the foot 5; all such systems are considered to be imaging systems and can be used with the present invention.

Referring to the Figures, the imaging platform assembly, generally designated 20, may be used to support the horse 3 during the foot imaging process. The platform assembly 20 includes a frame or platform 30 with a plurality of turntable assemblies 40 rotatably mounted to the platform 30. The platform 30, in one embodiment, is sized and configured to support the weight of horse 3, and provides a surface above the floor that the horse 3 can walk/stand partially or completely on. In one embodiment, the platform 30 has a lightweight construction with a baseplate 32 and suitable structural ribs or webbing 34 extending upward from the baseplate 32. An upper plate 35 is attached to the ribs 34 and forms a generally planar upper surface 36. This upper surface 36 is intended to directly engage the feet 5 of the horse 3 and therefore advantageously forms a flat continuous surface. If desired, the upper surface 36 may be perforated, such as being formed by so-called expanded steel, but such may not be desirable due to cleaning considerations. The upper surface 36 may include a suitable thin cushioning layer 39 that is advantageously resiliently deformable, and advantageously of an x-ray transparent material, as neoprene rubber. The platform 30 includes two upwardly-open recesses 38, which extend inward from the upper surface 36. These recesses are advantageously circular and spaced from one another by distance F. The platform 30 is advantageously generally rectangular, although any other convenient suitable shape may be alternatively employed. A plurality of adjustable feet 37 are advantageously mounted to the underside of the baseplate 32, so as to allow the platform 30 to be leveled when placed on uneven ground.

The turntable assemblies 40 are disposed in recesses 38. The turntable assemblies 40 include turntable decks 42 that are rotatably supported for rotation about their respective rotational axes 43. The turntable assemblies 40 are similar to each other, and advantageously identical. Turntable assembly 40, or simply turntable 40, includes an insertable turntable deck 42 and a bearing assembly 56. The turntable deck 42 has an upper surface 44 that is advantageously round, and corresponds in size to the opening of recess 38, with a small circumferential gap therebetween. The upper surface 44 may advantageously include a suitable thin cushioning layer 49, similar to that of the platform 30. The upper surface 44 is advantageously flush with the upper surface 36 of platform 30. A slot 50 is formed through the upper surface 44, forming an upwardly open trough for receiving and supporting the image capture device 12 in an upright fashion. The slot 50 is advantageously approximately one inch wide by fifteen inches long by one inch deep. The slot 50 extends along a slot centerline longitudinal axis 52, with that axis 52 advantageously offset from the corresponding rotational axis 43 by a distance D. Thus, the slot 50 is advantageously laterally offset relative to the center of the turntable deck's upper surface 44. The underside of the turntable deck 42 includes a smaller diameter flange 54 that acts as an alignment guide. Advantageously, both turntables 40 include slots, although only one turntable may have a slot in some embodiments. The bearing assembly 56 supports the turntable deck 42 for rotation relative to platform 30. The bearing assembly 56 may take any conventional load-bearing form, such as to ring-like plates interconnected by ball bearings. The center of the bearing assembly 56 is advantageously open for receiving the alignment flange 54 of the turntable deck 42. The bearing assembly 56 may be mounted directly to the baseplate 32 if desired.

To use the platform assembly 20, the platform 30 is placed on the floor, which may be unfinished ground. As indicated above, if the floor is uneven, the adjustable feet 37 may be adjusted as necessary to make the upper surface 36 of the platform 30 level and horizontal. If the turntable decks 42 have been removed, the turntable decks 42 are placed in their respective recesses 38, with the alignment guides 54 fitting into the respective bearing assemblies 56. In this fashion, the turntable decks 42 rest on the bearing assemblies 56 in a readily removable fashion, particularly for cleaning. The horse 3 is then led onto the platform 30 such that one of the feet 5 (front or rear) rests on the turntable decks 42. The other foot of the front/rear pair may rest on the area between the turntables 40. For illustrative purposes, it will be assumed that one or more of the rear feet 5 are to be imaged; as such, the a rear foot 5 is placed on a turntable 40, with the other rear foot 5 located in the area between the turntables 40, or on the other turntable 40, or outside of the other turntable 40. Note that the horse 3 is free to turn the foot 5 being imaged by simply rotating the turntable 40 without disengaging that foot 5 from the platform assembly 20. It is believed that this allowed movement mimics the way the feet 5 interact with a loose packed ground, and therefore feels natural to the horse 3. Because of this, applicant has discovered that the horse 3 is more likely to leave its feet 5 on the turntable 40 without additional movement after the initial rotation. Applicant further noticed that the horse 3 may shift its stance on any of its other three feet 5, yet the foot 5 on the turntable 40 will stay in the desired location because, it is believed, the rotation of the turntable 40 allows the horse 3 to feel comfortable without moving its foot 5 from the desired location on the turntable 40, thereby keeping the subject area of the foot 5 to be imaged positioned properly relative to the image capture device 12 (see below). Note also that the turntables 40 are independently rotatable, so that one turntable deck 42 may turn more or less than the other, or remain stationary if the horse 3 does not cause it to turn. Further, in embodiments where the upper surfaces 36, 44 of the platform 30 and the turntables 40 are similar, the horse 3 is advantageously unaware of standing on the platform 30 or standing on the turntable 40, except that the turntable 40 allows the foot 5 to rotate much like the foot 5 can rotate in dirt. The front feet 5 may be on the ground, or may be placed on another platform (or a different portion of an extended platform, see below), if desired.

The image capture device 12 is placed in the slot 50, advantageously after the horse 3 is positioned, but optionally before. The radiation source 10 is then placed on the other side of the foot 5 advantageously along a generally horizontal theoretical line L extending normal to the centerline 52 of slot 50 and through the rotational axis 43. This placement aligns the output radiation cone of the radiation source 10 perpendicular to the image capture device 12. Note that the radiation source 10 is located a suitable distance away from the foot 5, and at a suitable angle thereto, in accordance with the imaging system supplier's guidelines. The foot 5 is then imaged by passing the radiation through the foot 5 and to the image capture device 12. The image may then be analyzed for appropriate diagnosis/action.

When the imaging platform assembly 20 needs to be cleaned, such as to remove animal droppings, the upper surfaces 36, 44 may be sprayed and/or scrubbed clean. In addition, the turntable decks 42 may be removed and the corresponding recesses 38 sprayed and/or scrubbed clean. To facilitate cleaning, it may be advantageous for the edges of the imaging platform 30 to be open for easy drainage.

In some embodiments, a slot adapter (not shown) may be used to adapt the slot 50 for image capture devices 12 of varying sizes. For example, a somewhat U-shaped insert (not shown) may be placed in slot 50 and screwed into place in order to accommodate a thinner and/or shorter image capture device 12. Thus, the turntable assembly 40 may be adapted for use with image capture devices 12 of varying sizes.

Figure 5:
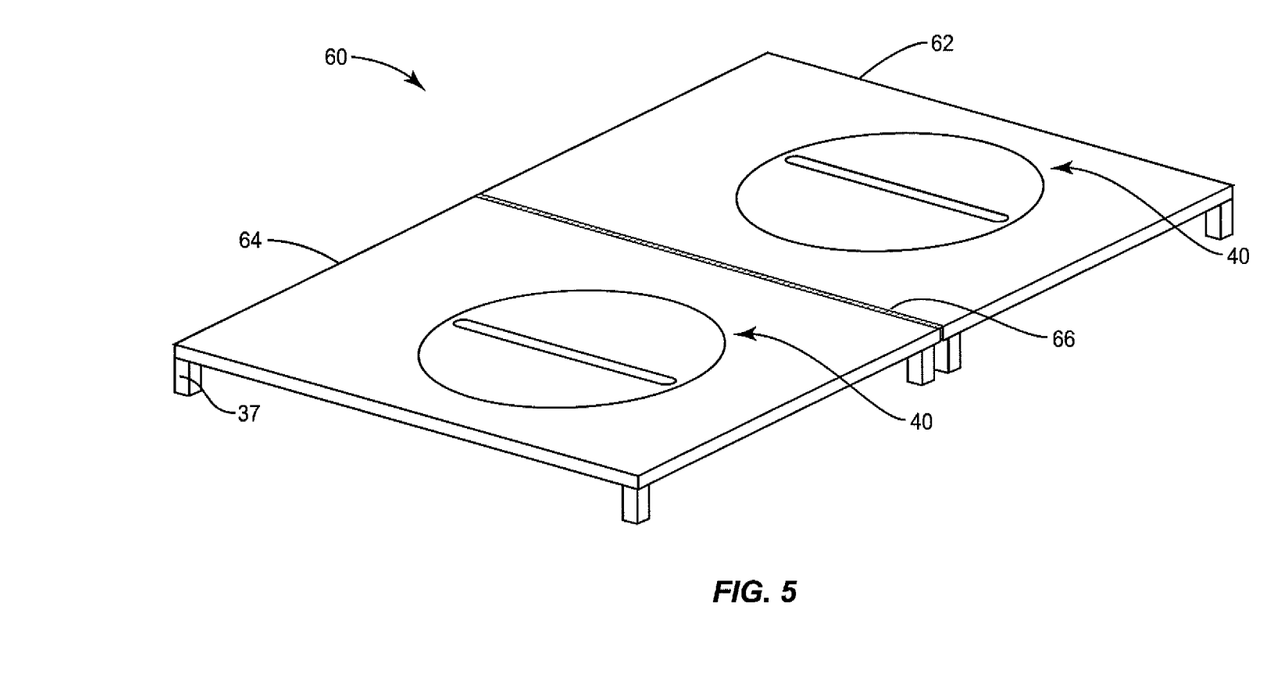
FIG. 5 shows one alternative embodiment of a foot imaging platform assembly.

Likewise, in some embodiments, the platform may be formed of sections that are hingedly coupled to allow the platform to be more easily stored and transported. For example, as shown in FIG. 5, platform 60 is similar to platform 30, but includes first and second lateral sections 62,64 that are hingedly connected by a hinge 66 disposed between the recesses 38, with each section 62,64 having a corresponding recess 38. In addition, each section 62,64 advantageously includes corresponding adjustable feet 37 on the underside thereof, with the opposing underside having suitable recesses (not shown) for accepting the feet 37 of the other section when the sections 62,64 are folded back to back.

Figure 1:
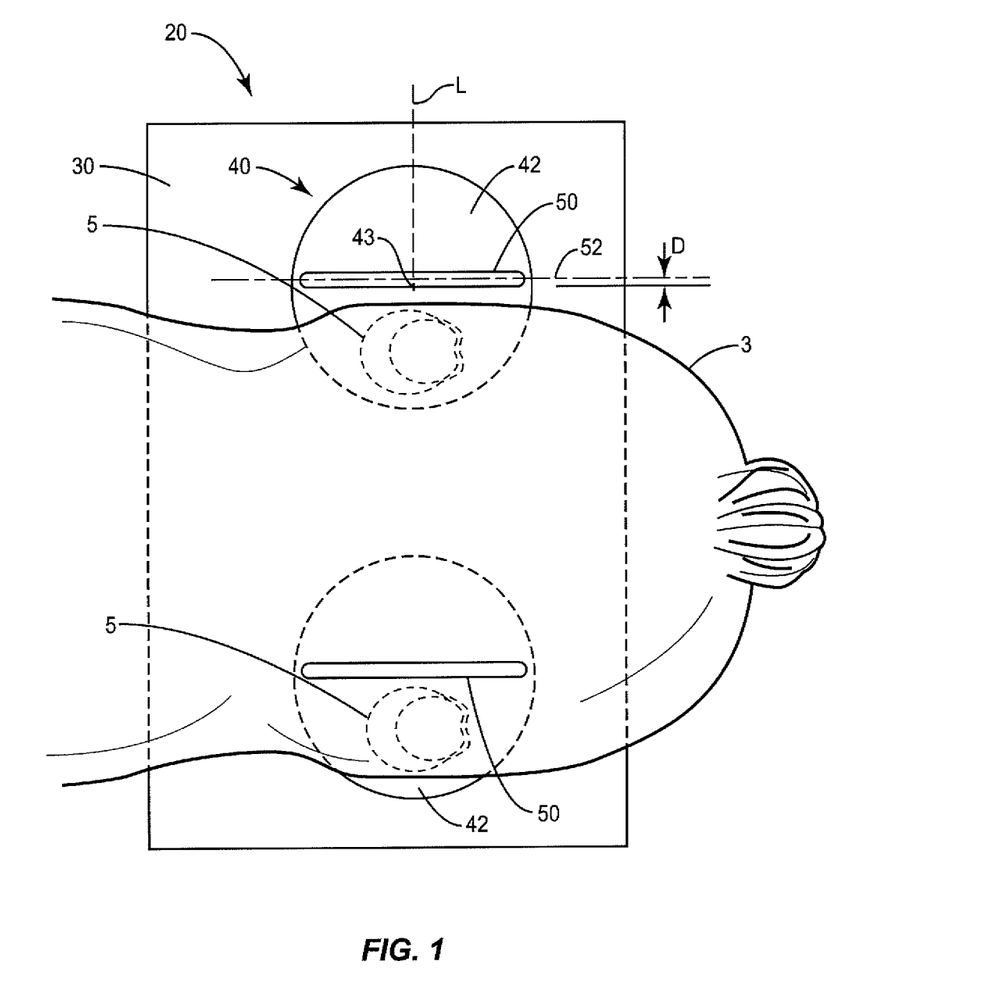
FIG. 1 shows a horse on its rear feet on a foot imaging platform assembly according to one or more embodiments of the present invention.
Figure 2:
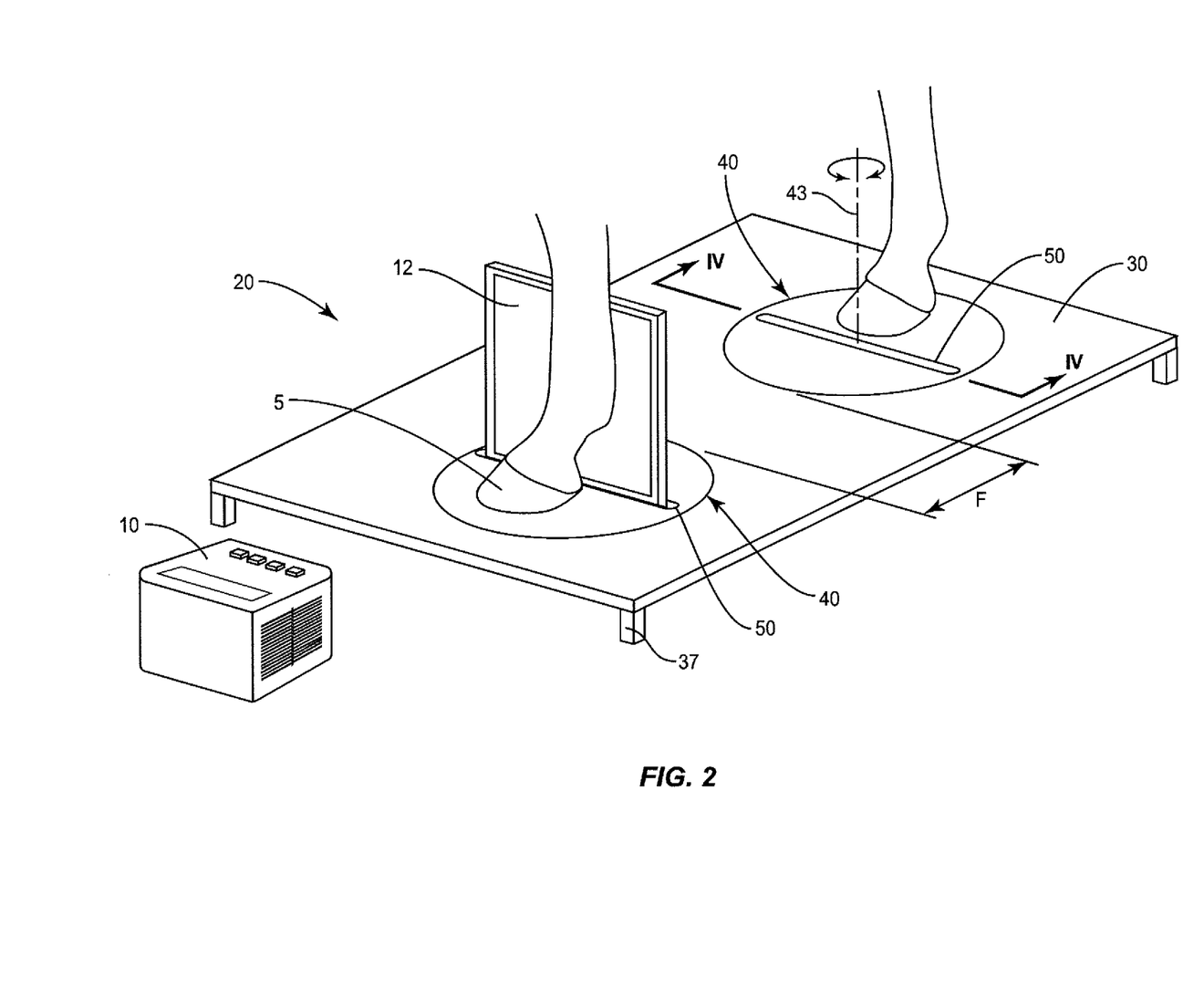
FIG. 2 shows a perspective view of the foot imaging platform assembly of FIG. 1.
Figure 3:
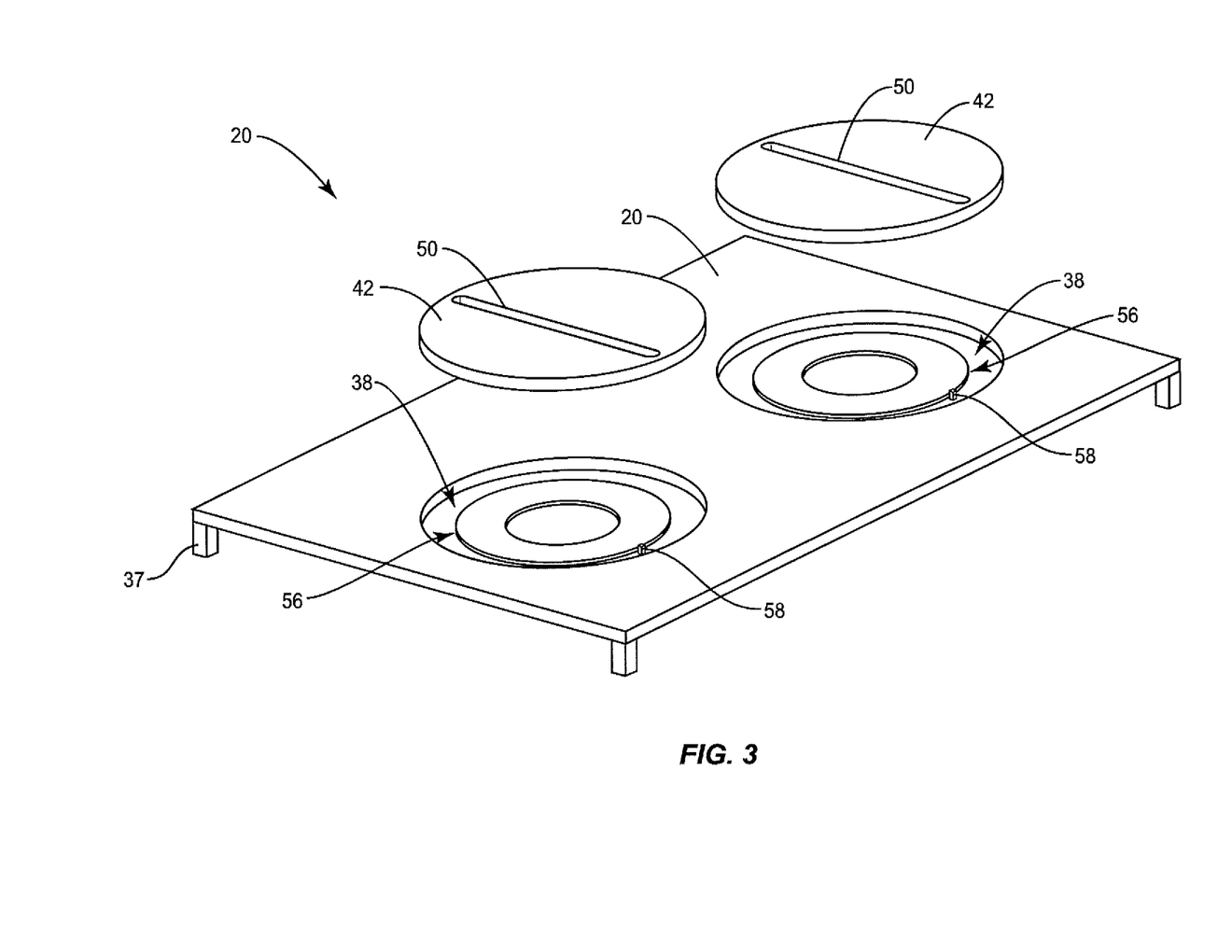
FIG. 3 shows a partially exploded view of the foot imaging platform assembly of FIG. 2.
Figure 4:
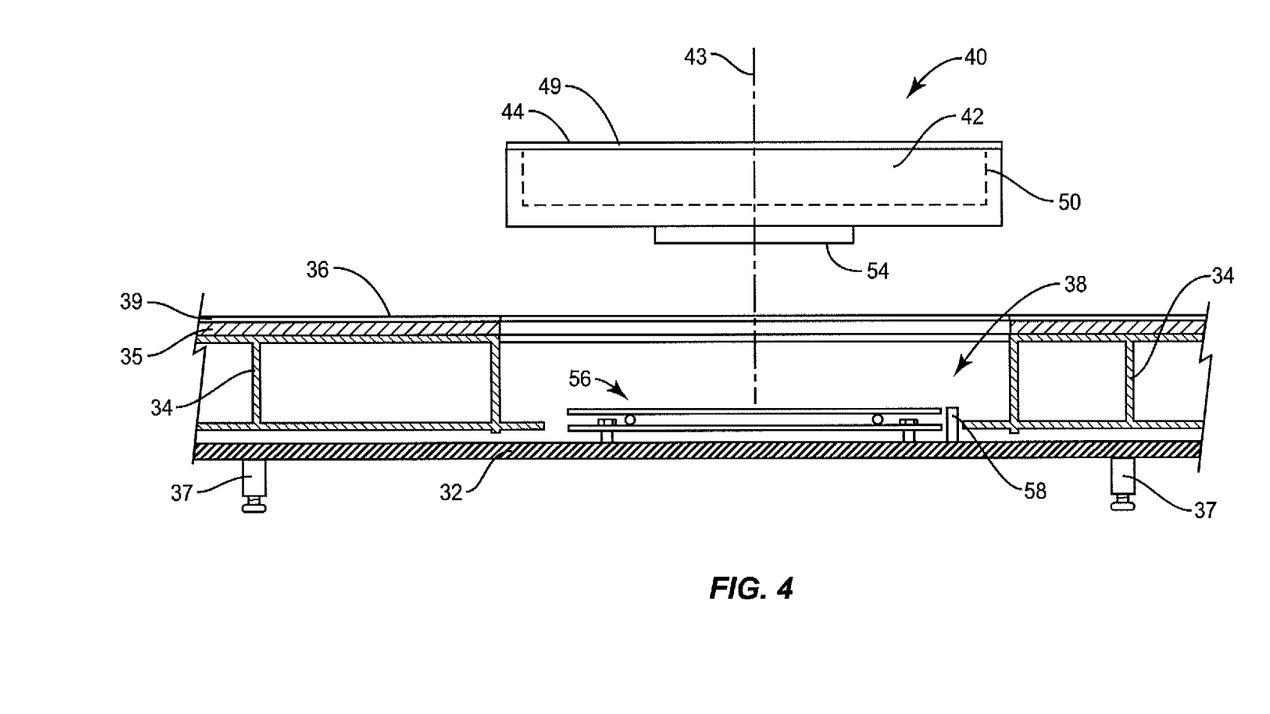
FIG. 4 shows a partially exploded cross-sectional view of the foot imaging platform assembly of FIG. 2 along line IV-IV.
Figure 6:
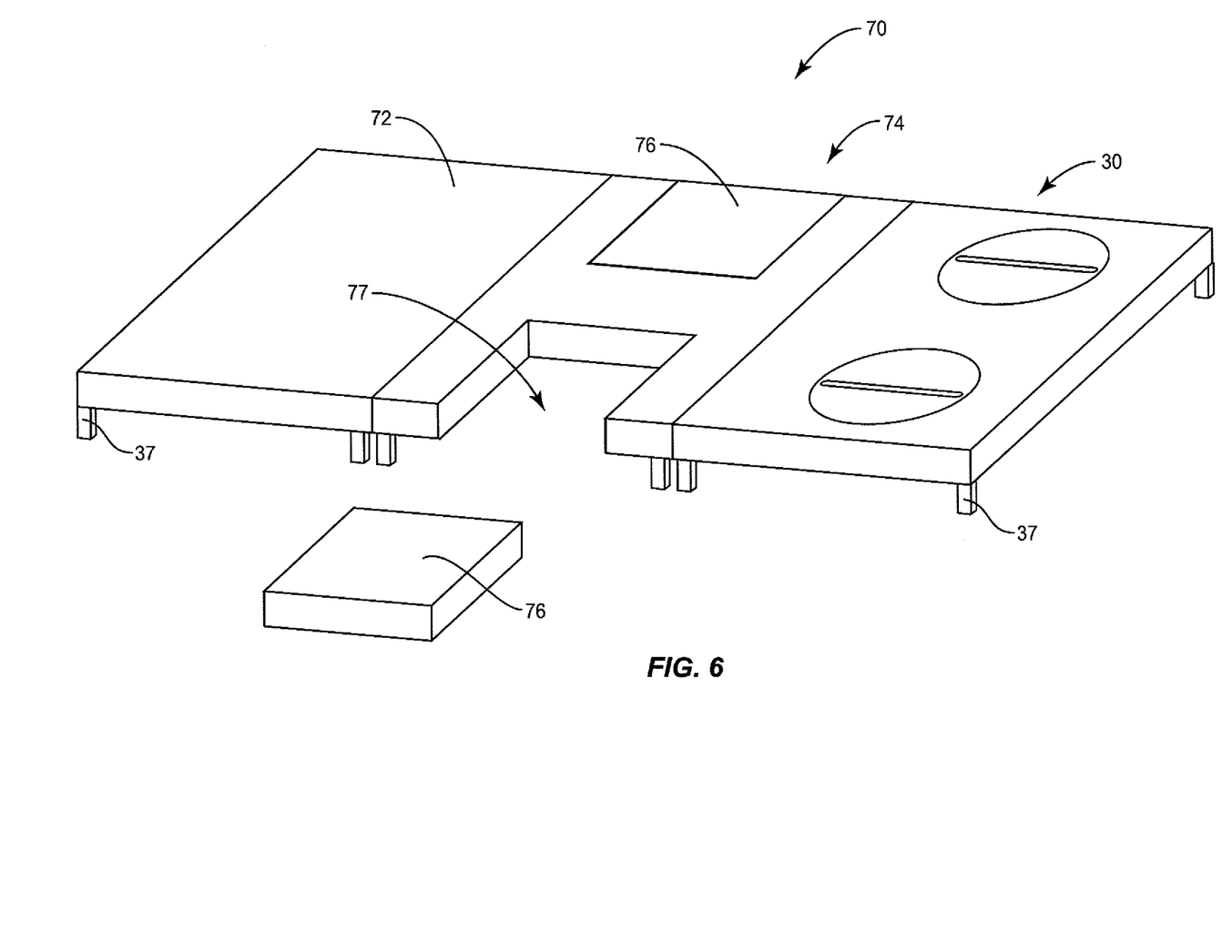
FIG. 6 shows another alternative embodiment of a foot imaging platform assembly.

In other embodiments, the platform 30 may be longitudinally extended so that it can support all four feet 5 of the horse 3. For example, as shown in FIG. 6, a multi-section platform 70 has additional panels, such as two additional panels 72,74. The panels are advantageously interlocking along their edge. The rear panel may be the platform 30 of FIG. 2. The front panel 72 may be a simple panel with a flat upper surface disposed at a suitable height. The middle panel 74 may also be a simple panel with a flat upper surface, or may advantageously include removable panel sections 76 that, when removed, expose suitable wells 77 for receiving the radiation source 10 when it is desired to take a "straight on" image of the foot 5 (i.e., front to back or back to front). Note that with the extended length platform assembly 70, the horse 3 is standing with both its front feet 5 and rear feet 5 on a level essentially continuous surface. As such, use of the extended multi-section platform assembly 70 allows the horse to stand on a level surface front and back when imaged, which is believed to result in better capture of the "real world" actual loading geometry on the foot. In some embodiments of the longitudinally extended platform assembly 70, the front section 72 may also include turntables 40, although such may be merely redundant because imaging of the front feet 5 can be accomplished by simply turning the horse 3 around such that front feet 5 rest on the turntables 40 of the rear panel 30.

Sometimes, it may be desirable to measure the amount of rotation that horse 3 imparts to the turntable 40. As such, some embodiments may include means for monitoring the amount of rotation. Such means may include, for example, suitable reference marks and angular gradations (not shown) on the turntable 40 and platform 30 such that the amount of angular displacement may be manually determined. Alternatively, the bearing assembly 56 may include a suitable electronic sensor 58 and output/display for monitoring the amount of angular displacement.

As can be appreciated, the platform assembly 20 should be constructed sturdy enough to support the weight of the animal being imaged. For example, the platform assembly 20 should be sturdy enough so as to withstand a six hundred pound weight per foot 5 without damage, whether placed on the platform 30 or on a turntable 40. The materials should be chosen accordingly, with stainless steel, aluminum, and polymers (such as polypropylene, polycarbonate, nylon) being believed to be among the suitable materials. In one embodiment, the baseplate 32 is thirty-two inches by forty-eight inches and formed of ¼ inch aluminum; the ribs 34 are aluminum channels of ⅛ inch thickness, 1½ inch in height, welded to the baseplate 32; the upper plate 35 is ⅛ thick aluminum, with a cushion layer 39 of 0.06 inch thick neoprene is adhesively secured thereto; the turntable recesses 38 are sixteen inches in diameter and spaced apart twenty-six inches; the recesses 38 extend downward to the baseplate 32; the bearing assemblies 56 are model number "kit8999" available from VXB Bearings of Anaheim, Calif.; the turntables 40 are formed from polypropylene and include a fifteen inch slot 50 of one inch width and one inch depth that is disposed immediately to one side of the rotational axis 43 at center of the turntable 40.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method of imaging an equine foot, comprising:
supporting both the front feet or both the rear feet of an equine animal on respective rotatable first and second turntables; the first and second turntables mounted to a common platform and rotatable independently of each other about respective rotational axes;
wherein the supporting comprises allowing the equine animal to rotate at least one of the first and second turntables;
wherein the first turntable has an upwardly open first slot therein;
placing an image capture device in the first slot of the first turntable;
thereafter, imaging the foot disposed on the first turntable by passing radiation through the foot to the image capture device.

2. The method of claim 1 wherein the second turntable has an upwardly open second slot therein; the method further comprising:
placing an image capture device in the second slot;
thereafter, imaging the foot disposed on the second turntable by passing radiation through the foot to the image capture device in the second slot.

3. The method of claim 1 wherein the platform has a generally planar upper surface;
wherein the first and second turntables have respective upper surfaces that are disposed generally flush with the upper surface of the platform.

4. The method of claim 1 wherein the supporting comprises disposing four feet of the equine animal on the platform, with two of the feet on the first and second turntables.

5. The method of claim 1 wherein the platform has adjustable legs and further comprising adjusting an orientation of an upper planar surface of the platform by adjusting one or more of the adjustable legs.

6. The method of claim 1 wherein the platform comprises first and second sections hingedly coupled together; wherein the first turntable is associated with the first section and the second turntable is associated with the second section; the method further comprising hinging the first section relative to the second section.

7. The method of claim 1 further comprising removing one or both of the first and second turntables from the platform.

8. The method of claim 1 further comprising removing a removable panel from the platform to expose a recess;

wherein the imaging comprises disposing a radiation source in the recess prior to the passing of radiation through the foot.

9. The method of claim 1 further comprising disposing, prior to said imaging, a radiation source substantially along a line that is normal to a longitudinal axis of the slot and passing through the rotational axis of the corresponding turntable.

10. The method of claim 1 wherein the equine animal is selected from the group consisting of a horse and a donkey.

11. An equine imaging platform assembly configured to support at least two feet of an equine animal, comprising:
a platform having a generally planar upper surface with first and second turntable recesses therein;
a first turntable disposed in the first recess and rotatably coupled to the platform for rotation about a first rotational axis; the first turntable having a first hoof-engaging turntable upper surface disposed generally flush to the upper surface of the platform;
a second turntable disposed in the second recess and rotatably coupled to the platform for rotation about a second rotational axis; the second turntable having a second hoof-engaging turntable upper surface disposed generally flush to the upper surface of the platform;
wherein the first and second rotational axis are spaced from one another and oriented generally normal to the platform upper surface;
the first turntable upper surface having an upwardly open first slot therein sized and configured to receive an image capturing device;
wherein the first and second turntables are rotatable independently of each other.

12. The equine imaging platform assembly of claim 11 wherein the platform comprises first and second sections hingedly coupled together; wherein the first and second recesses are disposed in the first and second sections respectively.

13. The equine imaging platform assembly of claim 11 wherein the first and second turntables are rotatably supported by respective bearing assemblies; wherein the first and second turntables are configured to be readily removable from the corresponding bearing assemblies without tools.

14. The equine imaging platform assembly of claim 11 wherein the first slot is offset from the first rotational axis.

15. The equine imaging platform assembly of claim 11 wherein the platform upper surface and the first and second turntable upper surfaces have non-slip layers thereon.

16. The equine imaging platform assembly of claim 11 wherein the first and second turntables are configured to support at least 600 pounds each.

17. The equine imaging platform assembly of claim 11 wherein the platform is sized to support the front feet of the equine animal when the turntables are supporting the rear feet of the equine animal.

18. The equine imaging platform assembly of claim 11 wherein the platform includes at least one removable panel disposed in spaced relation to the turntables.

* * * * *